United States Patent [19]

Yafuso et al.

[11] Patent Number: 5,175,016

[45] Date of Patent: Dec. 29, 1992

[54] METHOD FOR MAKING GAS SENSING ELEMENT

[75] Inventors: Masao Yafuso, El Toro; Mark Z. Holody, Irvine; Thomas P. Maxwell, Santa Ana; Thomas G. Hacker, Anaheim, all of Calif.

[73] Assignee: Minnesota Mining and Manufacturing Company, St. Paul, Minn.

[21] Appl. No.: 496,560

[22] Filed: Mar. 20, 1990

[51] Int. Cl.$^5$ .................. G01N 1/00; B05D 1/36
[52] U.S. Cl. ........................ 427/2; 427/389.7; 427/407.2; 422/82.05
[58] Field of Search ............ 422/58, 68.1, 82.07, 422/82.06, 82.08, 82.09; 436/68, 163, 165, 172; 128/634; 350/96.29, 96.30, 96.33; 356/39; 250/227.14; 427/2, 389.7, 407.2

[56] References Cited

U.S. PATENT DOCUMENTS

| | | | |
|---|---|---|---|
| Re. 31,879 | 5/1985 | Lubbers et al. | |
| 2,629,399 | 2/1953 | Kulick | 604/118 |
| 3,335,715 | 8/1967 | Hugenholtz et al. | 128/634 |
| 3,433,935 | 3/1969 | Sherman | 364/413.01 |
| 3,461,856 | 8/1969 | Polanyi | 128/633 |
| 3,498,286 | 3/1970 | Polanyi et al. | 128/634 |
| 3,512,517 | 5/1970 | Kadish et al. | 128/635 |
| 3,529,591 | 9/1970 | Schuette | 128/692 |
| 3,612,866 | 10/1971 | Stevens | 250/71 |
| 3,616,409 | 10/1971 | Tosteson | 204/195 |
| 3,658,053 | 4/1972 | Fergusson et al. | 128/632 |
| 3,674,013 | 7/1972 | Polanyl | 128/634 |
| 3,725,658 | 4/1973 | Stanley et al. | 250/364 |
| 3,807,390 | 4/1974 | Ostrowski et al. | 128/634 |
| 3,814,081 | 6/1974 | Mori | 128/634 |
| 3,822,695 | 7/1974 | Takayama | 128/634 |
| 3,841,308 | 10/1974 | Tate | 128/772 |
| 3,865,548 | 2/1975 | Padawer | 436/165 |
| 3,866,599 | 2/1975 | Johnson | 128/634 |
| 3,878,830 | 4/1975 | Bicher | 128/635 |
| 3,893,448 | 7/1975 | Brantigan | 128/632 |
| 3,904,373 | 9/1975 | Harper | 422/57 |
| 3,983,864 | 10/1976 | Sielaff et al. | 128/632 |
| 4,008,717 | 2/1977 | Kowarski | 128/632 |
| 4,016,864 | 4/1977 | Sielaff et al. | 128/632 |
| 4,050,450 | 9/1977 | Polanyi | 128/634 |
| 4,073,297 | 2/1978 | Kopp | 604/44 |
| 4,187,856 | 2/1980 | Hall et al. | 128/635 |
| 4,194,877 | 3/1980 | Peterson | 8/526 |
| 4,200,110 | 4/1980 | Peterson et al. | 128/634 |
| 4,201,222 | 5/1980 | Haase | 128/634 |

(List continued on next page.)

FOREIGN PATENT DOCUMENTS

| | | |
|---|---|---|
| 0105870 | 4/1984 | European Pat. Off. |
| 0276977 | 1/1988 | European Pat. Off. |
| WO84/01109 | 9/1983 | PCT Int'l Appl. |
| 1593270 | 11/1976 | United Kingdom |
| 2132348A | 7/1984 | United Kingdom |

OTHER PUBLICATIONS

New Riverside University Dictionary, Houghton Mifflin Company, 1984, p. 474.

IEEE Transactions on Biomedical Engineering, vol. BME-33, No. 2, "Optical Fluorescence and Its Application to an Intravascular Blood Gas Monitoring System", pp. 117-132, IEE, New York, J. L. Gehrich et al (Feb. 1986).

Zhujun et al, Analytica Chimica Acta 160, (1984), pp. 305-309.

Primary Examiner—Robert J. Warden
Assistant Examiner—T. A. Trembley
Attorney, Agent, or Firm—Frank J. Uxa, Jr.; Gordon L. Peterson

[57] ABSTRACT

A method for making a sensing element, and an assembled sensing element, useful in sensing the concentration of a gas, e.g., carbon dioxide, in a medium, e.g. blood, are disclosed. In one embodiment, the method comprises placing a quantity of a sensing composition precursor between and in contact with a transparent, gas impermeable solid disc and an opaque, gas permeable film, the sensing composition precursor comprises a sensing component, a polymer precursor and a crosslinking agent; and forming a gas sensing composition from this quantity of sensing composition precursor.

25 Claims, 1 Drawing Sheet

U.S. PATENT DOCUMENTS

| | | | |
|---|---|---|---|
| 4,210,029 | 7/1980 | Porter | 73/705 |
| 4,265,249 | 5/1981 | Schindler et al. | 128/635 |
| 4,274,417 | 6/1981 | Delpy | 128/632 |
| 4,295,470 | 10/1981 | Shaw et al. | 128/634 |
| 4,311,137 | 1/1982 | Gerard | 604/28 |
| 4,322,164 | 3/1982 | Shaw et al. | 356/243 |
| 4,340,615 | 7/1982 | Goodwin et al. | 427/2 |
| 4,398,542 | 8/1983 | Cunningham et al. | 128/675 |
| 4,399,099 | 8/1983 | Buckles | 422/58 |
| 4,407,290 | 10/1983 | Wilber | 128/633 |
| 4,471,765 | 9/1984 | Strauss et al. | 600/5 |
| 4,476,870 | 10/1984 | Peterson et al. | 128/634 |
| 4,476,877 | 10/1984 | Barker | 128/736 |
| 4,478,222 | 10/1984 | Koning et al. | 128/632 |
| 4,487,206 | 12/1984 | Aagard | 73/705 |
| 4,502,488 | 3/1985 | Degironimo et al. | 128/692 |
| 4,508,123 | 4/1985 | Wyatt et al. | 128/692 |
| 4,509,522 | 4/1985 | Manuccia et al. | 128/634 |
| 4,535,786 | 8/1985 | Kater | 128/760 |
| 4,543,961 | 10/1985 | Brown | 128/667 |
| 4,548,907 | 10/1985 | Seitz | 436/163 |
| 4,557,900 | 12/1985 | Heitzmann | 422/55 |
| 4,560,248 | 12/1985 | Cramp et al. | 350/96.34 |
| 4,573,968 | 3/1986 | Parker | 604/67 |
| 4,577,109 | 3/1986 | Hirschfeld | 250/461.1 |
| 4,585,007 | 3/1986 | Uchigaki et al. | 128/632 |
| 4,587,101 | 5/1986 | Marsoner et al. | 422/56 |
| 4,601,706 | 7/1986 | Aillon | 604/122 |
| 4,608,996 | 9/1986 | Brown | 128/760 |
| 4,640,820 | 2/1987 | Cooper | 422/82.04 |
| 4,651,741 | 3/1987 | Passafaro | 128/633 |
| 4,657,736 | 4/1987 | Marsoner et al. | 422/56 |
| 4,684,245 | 8/1987 | Goldring | 356/41 |
| 4,718,423 | 9/1988 | Willis et al. | 128/634 |
| 4,736,748 | 3/1988 | Nakamura et al. | 128/632 |
| 4,774,955 | 10/1988 | Jones | 128/632 |
| 4,775,514 | 10/1988 | Barnikol et al. | 422/82.08 |
| 4,785,814 | 11/1988 | Kane | 128/634 |
| 4,786,474 | 11/1988 | Cooper | 422/82.09 |
| 4,798,738 | 1/1989 | Yafuso et al. | 427/2 |
| 4,801,551 | 1/1989 | Byers et al. | 436/133 |
| 4,803,049 | 2/1989 | Hirschfeld et al. | 422/58 |
| 4,810,655 | 3/1989 | Khalil et al. | 436/138 |
| 4,824,789 | 4/1989 | Yafuso et al. | 436/68 |
| 4,830,013 | 5/1989 | Maxwell | 128/637 |
| 4,833,091 | 5/1989 | Leader et al. | 436/133 |
| 4,849,172 | 7/1989 | Yafuso et al. | 422/55 |
| 4,851,195 | 7/1989 | Matthews | 422/82.07 |
| 4,886,338 | 12/1989 | Yafuso et al. | 128/634 |
| 4,919,891 | 4/1990 | Yafuso et al. | 427/2 |
| 4,925,268 | 5/1990 | Iyer et al. | 350/96.29 |
| 4,965,087 | 10/1990 | Wolfbeis et al. | 436/163 |
| 4,989,606 | 2/1991 | Gehrich et al. | 128/637 |
| 4,999,306 | 3/1991 | Yafuso et al. | 422/82.07 |
| 5,000,901 | 3/1991 | Iyer et al. | 264/299 |
| 5,030,420 | 7/1991 | Bacon et al. | 128/634 |

U.S. Patent  Dec. 29, 1992  5,175,016
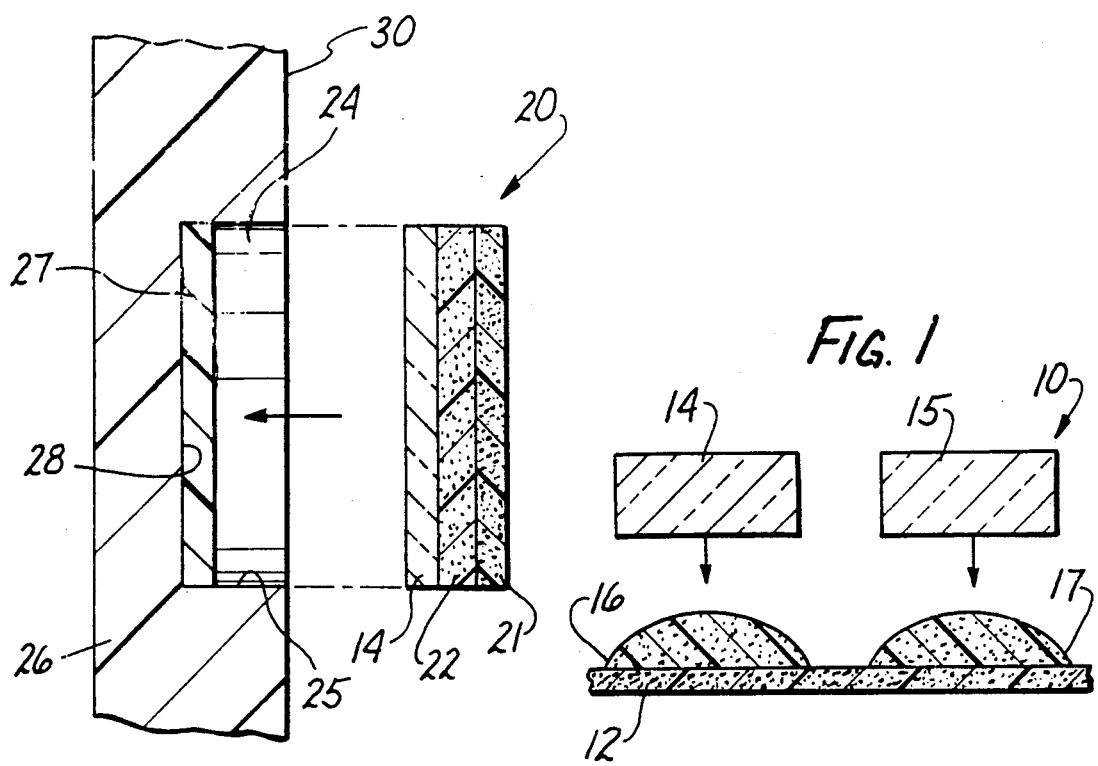
FIG. 1
FIG. 2
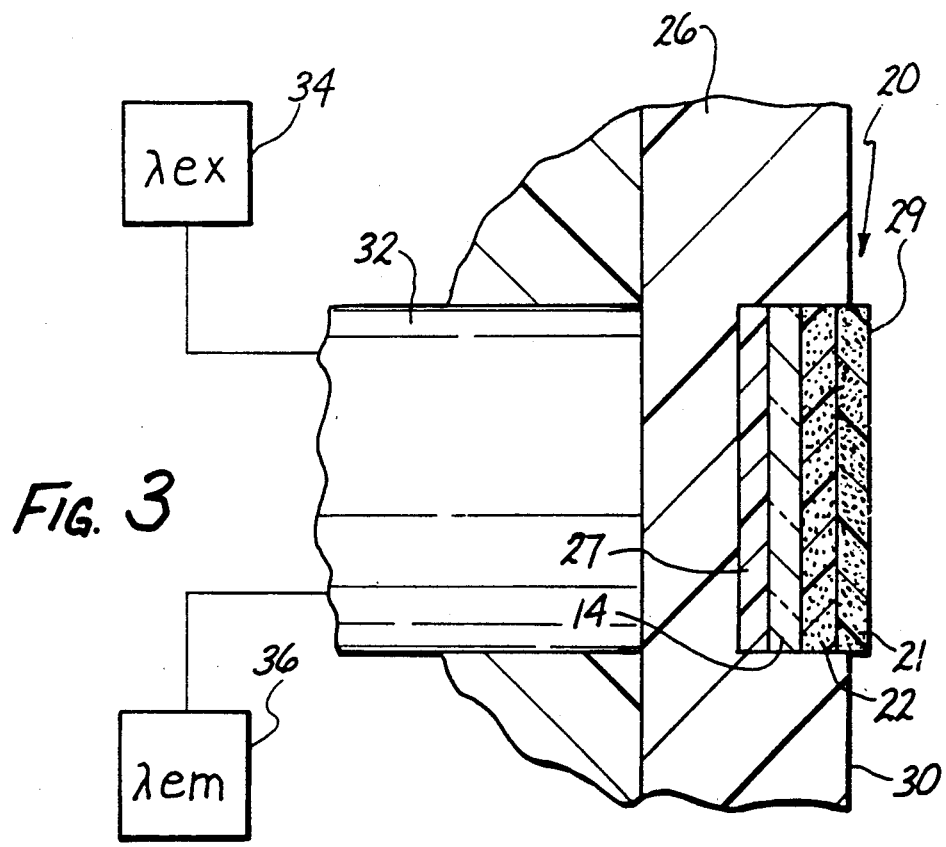
FIG. 3

METHOD FOR MAKING GAS SENSING ELEMENT

BACKGROUND OF THE INVENTION

This invention is related to gas sensing elements useful in sensing the concentration of a gas in a medium, and to methods for making such sensing elements. In particular, the invention relates to gas sensing elements useful in sensing the concentration of a gas, for example, carbon dioxide, in an aqueous medium, for example, blood.

In many situations, it is useful to determine the concentration, e.g. partial pressure, of a gas in a medium, e.g., a fluid medium. One such situation is the determination of the concentration of gas, e.g., carbon dioxide, oxygen and the like, in blood. Substantial recent interest has been focused on performing such determinations on a real time basis so that the current status of the patient being treated can be effectively monitored. Fluorescence-based sensors have been utilized to accomplish real time blood gas sensing. For example, fluorescence-based sensors can be used in an extracorporeal blood loop as shown in Cooper U.S. Pat. No. 4,640,820 and in vivo as disclosed in Lubbers et al Reissue U.S. Pat. No. 31,879. Each of these patents is incorporated by reference in its entirety herein.

Yafuso et al U.S. Pat. 4,824,789 discloses a sensing composition and sensor useful for determining the concentration of a gas in blood. This patent discloses a sensing composition which is useful when placed on the optical surface of an optical fiber to form a sensor. The sensing composition comprises an aqueous first phase dispersed in a cross-linked polymeric second phase. The aqueous first phase includes a dye, for example a pH sensitive dye. The crosslinked polymeric second phase, which is gas permeable and ion impermeable, preferably is silicone-based includes a hydrophobic filler, such as hydrophobic fumed silica particles. These sensing compositions may further include one or more emulsification enhancement agents, such as water soluble dextran and polyvinyl alcohol. This patent discloses that a teflon sleeve is used on the optical fiber during manufacture of the sensor to retain the sensing composition precursor on the optical surface of the optical fiber. The sensor also includes an opaque overcoat, such as cellulose impregnated with carbon black, to optically isolate the sensing composition.

The use of disposable cassettes for blood analysis is of substantial current interest, for example, to eliminate crosspatient contamination and to keep more expensive components, e.g., optical and electronic components, of the sensor system from being exposed directly to blood. One disposable cassette system is disclosed in commonly assigned U.S. Pat. application Ser. No. 229,617, filed Aug. 8, 1988.

Such a disposable cassette includes an indent, well or cavity into which a sensing element is at least partially placed. The sensing element is exposed to blood and the sensing component, e.g., a fluorescent dye, gives off a signal which varies in response to variations in the concentration of the gas of interest in the blood. A signal transmitter, e.g., an optical fiber, spaced away from the cassette well and blood transmits this signal to a processor where it is analyzed to provide the desired blood gas concentration determination.

One problem which has presented itself with regard to the use of these cassettes is that of inconsistent and/or inaccurate blood gas concentration determinations. For example, such cassette blood gas sensors have exhibited "drift"; that is, the signal representing a certain given gas concentration varies or drifts over time. Also, when the sensing element is manufactured or assembled in situ, e.g., in the well of the cassette, there is no chance to screen the sensing element before it is bonded to the cassette. Thus, non-specification sensing elements can be included in the cassette and determined as being non-conforming only after the assembled cassette, which often includes a number of other sensing elements for different blood constituents, is tested. At this point, the entire cassette must be discarded, resulting in substantial waste and cost.

It would be clearly advantageous to provide new sensing elements and/or new methods for making sensing elements, particularly for use in such cassettes.

SUMMARY OF THE INVENTION

A new sensing element, and method for making a sensing element, useful in sensing the concentration of a gas, e.g., carbon dioxide, in a medium, e.g., blood, have been discovered. The present sensing elements provide substantial benefits. For example, these elements can be assembled, and then tested or screened, e g., to assure conformity to specifications, before they are included in the final sensor holder, e.g., cassette. This feature reduces the cost and time required to produce high quality sensors which provide reliable and consistent gas concentration determinations. Moreover, the present sensing elements preferably have a reduced tendency to be subject to signal "drift". The present method for producing sensing elements is straightforward and relatively easy to practice. The relative amount of non-specification sensing elements is reduced, and since the sensing element can be tested or screened before it is included with the other sensor components, the cost of producing non-specification sensing elements is even further reduced.

In one broad aspect, the present invention is directed to an assembled gas sensing element. This assembled element comprises a transparent, gas impermeable, solid disc, preferably made of glass; an opaque, gas permeable film, preferably including a polymer; and a quantity of a gas sensing composition located between and in contact with the solid disc and the film. This gas sensing composition comprises a gas permeable and light permeable polymeric material, and a sensing component. The assembled element is sized and adapted to be at least partially placed in a cavity or well, having one open end, in a sensor holder, e.g., cassette, after assembly. Thus, this assembled element can be tested and/or otherwise screened before it is included in the sensor. This "pre-screening" feature reduces the amount of waste caused by having an off specification sensing element. Thus, the unacceptable sensing element alone can be discarded rather than having to scrap the entire sensor cassette.

In another broad aspect of the present invention, a method for making a sensing element useful in sensing the concentration of a gas in a medium is provided. This method comprises placing a quantity of a sensing composition precursor between and in contact with a transparent, gas impermeable solid disc and an opaque, gas permeable film. The sensing composition precursor comprises a sensing component and a polymer precursor. A sensing composition is formed from this quantity of sensing composition precursor.

After the sensing element has been produced, and preferably screened or tested to determine its efficacy, the sensing element is preferably placed at least partially in a cavity or well, having an open end and preferably only one open end, located in a substantially transparent sensor holder. The sensing element is preferably oriented so that the film is exposed to the medium the gas concentration of which is being monitored and the face of the solid disc away from the sensing composition is substantially shielded from direct contact with this medium.

Further aspects of the present invention provide a new sensing composition precursor and a new sensing composition. The sensing composition precursor comprises a dispersed aqueous liquid including a sensing component dissolved therein, a polymer precursor, and a hydrophilic dispersing agent selected from hydroxyalkyl celluloses and mixtures thereof in an amount effective to facilitate maintaining the dispersed aqueous liquid. The sensing composition comprises a gas permeable and light permeable polymeric material, a dispersed aqueous liquid including a sensing component dissolved therein, and a hydrophilic dispersing agent selected from hydroxyalkyl celluloses and mixtures thereof in an amount effective to facilitate maintaining the aqueous liquid dispersed in the sensing composition precursor prior to forming the sensing composition. The use of hydroxyalkyl celluloses, in particular hydroxyethyl cellulose, rather than water soluble dextran or polyvinyl alcohol as taught in the prior art, may contribute to the substantial reduction in the tendency of the sensors, in particular the carbon dioxide sensors, of the present invention to be subject to signal "drift".

These and other aspects of the present invention are set forth in the following detailed description and claims, particularly when considered in conjunction with the accompanying drawings in which like parts bear like reference numerals.

BRIEF DESCRIPTION OF THE DRAWINGS

FIG. 1 is a cross sectional view showing an embodiment of the present sensing elements being assembled.

FIG. 2 is a cross sectional view showing an assembled sensing element being bonded to a sensor cassette.

FIG. 3 is a schematic view showing a sensing element bonded to the sensor cassette in use providing signals useful to sense the concentration of a gas in a medium.

DETAILED DESCRIPTION OF THE INVENTION AND DRAWINGS

The present invention is directed to an assembled gas sensing element, such as an assembled carbon dioxide sensing element or an assembled oxygen sensing element, useful in sensing the concentration of a gas in a medium, e.g., a fluid medium, in particular blood. This assembled sensing element comprises a transparent gas impermeable solid disc and an opaque gas permeable film. A quantity of a gas sensing composition is located between and in contact with both the solid disc and the film. This gas sensing composition comprises a gas permeable and light permeable, and preferably substantially ion impermeable, polymeric material, and a sensing component. When the sensing composition is useful in sensing carbon dioxide, it preferably includes a dispersed aqueous liquid including a sensing component dissolved therein. The aqueous liquid in the present sensing composition is preferably dispersed in microcompartments, more preferably in microcompartments having a maximum transverse dimension, e.g., diameter, of about 5 microns or less. The sensing component preferably provides a signal, more preferably an optical signal, which varies in response to variations in the concentration of the gas of interest in the medium being monitored. The assembled gas sensing element is sized and adapted to be at least partially placed into a cavity or well having one, and preferably only one, open end and being located in a sensor holder, preferably a sensor cassette, after assembly.

The present sensing elements preferably have a reduced tendency to be subject to signal "drift". In particular, this reduced tendency is apparent in the present carbon dioxide sensing elements which are used to periodically monitor carbon dioxide concentration in blood as follows. Such carbon dioxide sensing elements are often stored in an environment having substantially no concentration of carbon dioxide. In use, the sensing elements are normally exposed to saline or other materials which include little or no carbon dioxide. Blood, having a concentration (partial pressure) of carbon dioxide in the physiological range, e.g., between about 20 and 60 mm Hg., is contacted with the sensing elements for up to about 5 minutes each time a concentration determination is to be made. It is in this particularly difficult use that the present sensing elements preferably show a reduced tendency to be subject to signal "drift".

The solid disc is transparent and gas impermeable. Thus, the solid disc allows the signal, preferably the optical signal, from the sensing component to pass through, while reducing or even substantially eliminating diffusion of the gas of interest from the medium being monitored into the sensor holder. Such diffusion is disadvantageous since it may detract from the accuracy of the gas concentration determined. One particularly useful material of construction for this solid disc is glass. The solid disc preferably includes opposing end surfaces, spaced apart by the thickness of the disc, which are substantially mutually parallel. The disc is preferably shaped to at least partially fit into the cavity of the sensor holder, as described herein, e.g., with one end surface facing the wall opposite the open end of the sensor holder cavity or well. The disc can have the configuration of a right circular cylinder. In one embodiment, the disc has a thickness in the range of about 0.005 inches to about 0.1 inches, and preferably a diameter in the range of about 0.05 inches to about 0.5 inches.

The film is opaque and gas permeable. This film acts to provide a substantial degree of optical isolation for the sensing composition. This optical isolation allows a substantially focused or directed signal from the sensing component to be transmitted for analysis, as described hereinafter, with reduced interference, e.g., from other sensing elements in the cassette. Ultimately, such optical isolation results in increased accuracy and reliability of the gas concentration determinations obtained using the present sensing elements. The film should be freely permeable to the gas of interest in the medium being monitored. This gas permeability allows the gas of interest from the medium to contact the sensing composition and interact with the sensing component. The film is preferably made from a polymer combined with an opaque agent.

Any suitable polymer may be included in the presently useful film, provided that the polymer has no substantial detrimental effect on the functioning of the present system or on the medium being monitored. The polymer chosen preferably provides a relatively thin film with sufficient structural integrity and durability to be useful in the present methods of producing sensing elements, as well as in use sensing gas concentrations as part of the final sensing element. In one particularly useful embodiment, the film includes a fluorine-containing polymer, preferably a polymer selected from polyfluorohydrocarbons, polyfluorocarbons and mixtures thereof, and especially, polytetrafluoroethylene. Preferably, the film is substantially thinner than the solid disc, e.g., to facilitate gas permeability. More preferably, the thickness of the film is in the range of about 1% to about 20% of the thickness of the solid disc. Like the solid disc, the film preferably includes opposing end surfaces which are substantially mutually parallel. Such end surfaces are preferably shaped to be compatible with the shape of the solid disc and with the shape of the cavity of the sensor holder. Such end surfaces may be circular. In one embodiment, the film has a thickness in the range of about 0.0001 inches, or less, to about 0.001 inches, or more, preferably about 0.0002 inches to about 0.0006 inches.

Any suitable opaque agent may be used provided that such agent or agents function to provide the desired degree of optical isolation and have no substantial detrimental effect on the functioning of the present system or on the medium being monitored. Among the opaque agents useful in the present invention are carbon black, other carbon based opaque agents, ferric oxide, metallic phthalocyanines and the like. Such opaque agents are preferably substantially uniformly dispersed in the film in an amount effective to provide the desired degree of opacity, e.g., to provide the desired optical isolation. A particularly useful opaque agent is carbon black.

The polymeric material of the gas sensing composition is permeable to the gas of interest in the medium being monitored and is permeable to the wave lengths of light utilized in the measurement of the concentration of this gas. Further, if the sensing composition is to be used in sensing carbon dioxide, this polymeric material is preferably impermeable to ions and to liquid water. For example, if the sensing component is dissolved in a dispersed aqueous liquid and, as is preferred, the aqueous liquid contains a buffer, the concentration of the buffer ions is preferably maintained substantially constant so that the sensing composition provides consistent signals in response to the concentration of the gas of interest in the medium.

Any suitable polymeric material may be employed in the present gas sensing compositions provided that the polymeric material has no substantial detrimental effect on the functioning of the present system or on the medium being monitored. Because of substantial gas and light permeability and aqueous impermeability properties, silicone-based polymeric materials are preferred. More preferably, crosslinked silicone-based polymeric materials are employed. When the gas of interest is carbon dioxide or oxygen, the polymeric material is preferably cross-linked polydimethyl siloxane. The precursor of the polymeric material, hereinafter referred to as the polymer precursor, may be selected from one or more monomers, pre-polymers, and mixtures thereof. A particularly useful polymer precursor, e.g., when carbon dioxide or oxygen is the gas of interest, is vinyl terminated dimethyl siloxane, such as that sold by Petrarch Systems under the trademark PS 443. If the polymeric material is to be cross-linked, a cross-linking agent is included with the polymer precursor. Such cross-linking agents are preferably compounds which include at least two functional groups capable of reacting with the polymer precursor and/or a partially polymerized intermediate to form cross links, e.g., between polymer chains, in the polymeric material. A particularly useful cross-linking agent is methylhydro-dimethylsiloxane copolymer, such as that sold by Petrarch Systems under the trademark PS 123, especially when the polymer precursor includes vinyl terminated dimethylsiloxane. One or more catalysts may be used to promote the formation of the polymeric material. One such catalyst is platinum. An example of a platinum-containing catalyst material is sold by Petrarch Systems under the trademark PC072. The amount of catalyst used should be sufficient to promote the desired degree of polymerization. Of course, the catalyst should have no substantial detrimental effect on the functioning of the present system or on the medium being monitored.

Alternately, the silicone-based polymeric material can be formed through condensation polymerization reactions with silanol terminated silicones being cross-linked with alkoxyl silanes using catalysts, such as tin derivatives.

Fillers can be, and preferably are, included in the present gas sensing compositions which include dispersed aqueous liquid. Such fillers act to enhance the stability of the dispersed aqueous liquid in the sensing composition and the strength of the sensing composition. Any suitable filler may be used provided it has no substantial detrimental effect on the functioning of the present system or on the medium being monitored. In one embodiment, the filler has a hydrophobic nature. Such fillers are preferably present in an amount in the range of about 1% to about 20% by weight, based on the amount of polymeric material present in the gas sensing composition. A particularly useful filler is hydrophobic fumed silica, e.g., in the form of fine particles.

The sensing component or components chosen for use are those effective to provide a signal which varies in response to variations in the concentrations of the gas of interest in the medium being monitored. The sensing component is preferably an optical indicator, such as fluorescence indicators and absorbance indicators, in particular fluorescence indicators. In sensing carbon dioxide concentrations, examples of absorbance indicators that can be used include chlorophenyl red, bromo cresol purple, nitrophenol, bromo thymol blue, penachlorome, pheno red and the like. Useful fluorescence indicators for carbon dioxide include hydroxypyrene 3,6,8- trisulfonic acid, herein referred to as HPTS or hydroxypyrene trisulfonic acid, derivatives, e.g., salts, of HPTS, beta-methylumbelliferone, fluorescein and the like. The more preferred sensing component, particularly for sensing the concentration of carbon dioxide in blood, is selected from HPTS, derivatives of HPTS and mixtures thereof. The alkali and alkaline earth metal salts of HPTS are useful HPTS derivatives. Very pure sensing components, in particular laser grade HPTS and derivatives of laser grade HPTS, are very effective for producing carbon dioxide sensing elements which advantageously have a reduced tendency to be subject to signal drift over time. In sensing oxygen concentrations, examples of fluorescence indicators include one or more polynuclear aromatic compounds, derivatives of polynuclear aromatic compounds and the like. Examples of such polynuclear aromatic compounds include decacyclene, benzo-ghi-perylene and coronene. The oxygen indicators may include a mixture of tertiary butyl derivatives of such polynuclear aromatic compounds. Such indicators are more fully described in Yafuso, et al U.S. Pat. No. 4,849,172 which is incorporated by reference in its entirety herein.

The amount of sensing component used is such as to provide a sufficiently strong signal so that the concentration of the gas of interest can be reliably and accurately determined.

For sensing carbon dioxide, the aqueous liquid of the gas sensing composition is preferably buffered, more preferably using a carbonate ion and/or bicarbonate ion based buffer system. Such a buffer is preferably chosen so as to have a buffer range compatible with the response range of the sensing component. Such a range might, for instance, mimic the physiological pH range of blood. Any suitable buffer material may be employed to buffer the aqueous liquid, provided such material has no substantial detrimental effect on the functioning of the present system or on the medium being monitored. Examples of such materials include alkali metal carbonates, alkali metal bicarbonates and the like. The amount of buffer used is such as to provide the desired degree of buffering to the aqueous medium. For measuring blood carbon dioxide with hydroxypyrene trisulfonic acid, a pH range of about 6 to about 8 is desirable.

The present gas sensing composition precursors and gas sensing compositions which include an aqueous liquid preferably also include an effective amount of at least one hydrophilic dispersing agent. Such agents act to facilitate maintaining the aqueous liquid dispersed in the sensing composition precursor prior to forming the polymeric material. Thus, increases in shelf life of the sensing composition precursor are obtained. Also, these agents may act to retard dehydration of the aqueous liquid. Overall, such hydrophilic dispersing agents reduce the need to adhere to a tight manufacturing schedule in producing the assembled sensing elements of the present invention, and reduce the generation of manufacturing "scrap materials" which is economically wasteful.

Any suitable hydrophilic dispersing agent may be used provided that such agent has no substantial detrimental effect on the functioning of the present system or on the medium being monitored. Examples of hydrophilic dispersing agents include water-soluble dextran, polyvinyl alcohol and the like materials. The amount of hydrophilic dispersing agent utilized is not critical and may vary depending, for example, on the specific dispersing agent, polymer precursor and filler being employed. In one embodiment, the amount of dispersing agent present is in the range of about 1% to about 20% by weight of the total aqueous liquid employed.

One of the important preferred features of the present invention is the use of hydrophilic cellulosic dispersing agents rather than the water soluble dextran or polyvinyl alcohol suggested in the prior art, e.g., Yafuso et al U.S. Pat. No. 4,824,789. Such cellulosic agents, which are preferably water soluble, provide gas sensing elements which provide a consistent signal in response to a given concentration of gas in the liquid medium being monitored. The hydrophilic cellulosic materials used as dispersing agents are preferably hydroxyalkyl celluloses and mixtures thereof. The alkyl group may contain, for example, one to about five or more carbon atoms. A particularly useful dispersing agent is hydroxyethyl cellulose.

The precursor for the carbon dioxide sensing composition may be prepared as follows. The precursor for the oxygen sensing composition may be prepared in a somewhat analogous manner except that no aqueous liquid is used and an organic solvent is used to combine the sensing component into the polymer precursor. The carbon dioxide sensing component is dissolved in a quantity of liquid water to form an aqueous liquid. If desired, a buffer and/or hydrophilic dispersing agent can also be dissolved in this aqueous liquid. The desired amount of polymer precursor, and, if desired, a filler component and polymerization catalyst, is (are) mixed with the aqueous liquid. At this point, no cross-linking agent or agents are included.

The resulting mixture is subjected to strong agitation, e.g., in a mechanical homogenizer, to disperse the aqueous liquid and form a first sensing composition precursor. After this agitation, the first sensing composition precursor containing dispersed aqueous liquid can be stored for a period of time, e.g. on the order of about 1 hour to about 24 hours or more, ready for use in making the assembled gas sensing element.

When it is desired to form the gas sensing composition of the invention, the cross-linking agent or agents, if any, and the polymerization catalyst if not already present, are added to the first sensing composition precursor. These are gently stirred into the first sensing composition precursor to form the second or final gas sensing composition precursor.

After the final sensing composition precursor has been prepared, a quantity of it is placed on one side of a sheet of the opaque film. At least one solid disc is then placed on this quantity of final sensing composition precursor so that the final sensing composition precursor is located between and in contact with both the solid disc and the opaque film. Preferably, a plurality of such solid discs are so placed, more preferably placed spaced apart, on this sensing composition precursor. If a plurality of solid discs are used, the sensing composition precursor may be located in individual or discrete portions, e.g. drops, on the opaque film. In this embodiment, a plurality of gas sensing elements can be effectively produced from a single sheet of opaque film. The sensing composition precursor is then allowed to react, e.g., polymerize and/or cross-link, to form the sensing composition. The assembled sensing element can be obtained by removing, e.g, cutting, the solid disc, together with a portion of the sensing composition and a portion of the opaque film sheet from the remainder of the opaque film sheet. Additional processing, e.g., trimming, may be useful to substantially conform the shape of the opaque film and sensing composition components of the sensing element to the shape of the area of the solid disc in contact with the sensing composition component. The assembled gas sensing element can be tested and/or screened, using conventional techniques, to determine its efficacy in measuring the concentration of the gas of interest. Such tests, for example, may seek to determine the intensity of the signal provided by the assembled gas sensing element and/or the response time of the assembled gas sensing element to changes in the concentration of the gas of interest.

If the assembled gas sensing element is satisfactory, it is then placed at least partially in an open-ended cavity in a sensor holder. Preferably, the assembled sensing element is secured, e.g., by adhesive, to the sensor holder. The sensing element is situated relative to the sensor holder so that the solid disc is preferably located relatively near to and facing the bottom of the open-ended cavity and the opaque film is exposed to the medium being monitored.

The sensor holder is preferably placed in proximity to an optical fiber such that signals from the sensing composition can be transmitted by the optical fiber to a processor so that the concentration of the gas of interest in the medium can be determined based upon such signals.

The following non-limiting examples illustrate certain aspects of the present invention.

EXAMPLE 1

An aqueous solution was formed by dissolving 0.2 g of laser grade hydroxypyrene trisulfonate (trisodium salt), 0.25 g of sodium chloride, 0.042 g of sodium carbonate and 6.1 g of hydroxyethyl cellulose in 60 cc of water.

A silicone formulation was made by mixing 0.3 g of fine particles of hydrophobic fumed silica, sold by Tulco, Inc. under the trademark Tulanox 500, into 10 g of vinyl terminated dimethyl siloxane, sold by Petrarch Systems under the trademark PS 443. This mixture also included a trace amount (1 drop per 50 g of the vinyl terminated dimethyl siloxane) of a platinum-containing component (catalyst), sold by Petrarch Systems under the trademark PC 072.

2.0 g of the aqueous solution was combined with the silicone formulation and the mixture was homogenized in a Virtis 25 homogenizer. An amount of methylhydrodimethylsiloxane copolymer, sold by Petrarch Systems under the trademark PS 123, equal to about 10% by weight of the homogenized mixture was mixed with the homogenized mixture to form the sensing composition precursor.

A 10 cm by 10 cm sheet of an opaque film, about 0.0004 inches thick, was stretched on a frame or fixture. The opaque film was made from polytetrafluoroethylene mixed with carbon black and sold by Chemical Fabrics Corporation under the trademark DF-1100 Black teflon. Discrete drops of the sensing composition precursor was applied to the bondable side of the stretched sheet.

A right circular cylindrical transparent glass disc, about 0.012 inches thick and 0.120 inches in diameter, was placed on each drop of the sensing composition precursor, with a flat end directly contacting the precursor. These discs had previously been treated with allyl trimethoxy silane, a coupling agent, and a solution of platinum-containing catalyst in hexane. With the discs in place, the resulting composite was allowed to stand overnight at room temperature and then the vinyl terminated dimethyl siloxane and methylhydrodimethylsiloxane copolymer mixture was further cured for about 90 minutes at 65° C. to form a sensing composition comprising cross-linked silicone-based polymer with dispersed microcompartments of the aqueous solution.

Individual carbon dioxide sensing elements were cut from the glass discs/sensing composition/sheet composite. Each sensing element included one glass disc, a generally circularly shaped portion of an opaque film and a thin layer of the sensing composition therebetween. The sensing element was trimmed to more closely conform the opaque film and the layer of sensing composition to the circular shape of the glass disc. The end of the glass disc not in contact with the sensing composition were washed with methanol.

Using conventional testing procedures, each of the assembled carbon dioxide sensing elements is tested to determine its efficacy for accurately and reliably sensing the concentration of carbon dioxide in human blood. These assembled carbon dioxide sensing elements are found to be satisfactory based on this testing procedure.

Using a transparent silicone-based adhesive, one of these carbon dioxide sensing elements is bonded into a right circular cylindrical open ended well, having a diameter of 0.125 inches and a depth of 0.010+0.001 inches, formed in a polycarbonate cassette. The glass disc is facing the bottom of the well. Prior to bonding the sensing elements to the cassette, the walls of the well are contacted with a priming agent, sold by Dow Chemical Company under the trademark Dow 1205, to promote adhesion between the sensing element and the polycarbonate cassette.

The thus produced carbon dioxide sensor is effective in determining the concentration of carbon dioxide in blood brought into contact with the film.

FIGS. 1, 2 and 3 illustrate the manufacture of a sensing element as described in the above Example, and its use in determining gas concentrations. In FIG. 1, the relative thicknesses of the glass discs and opaque film are somewhat accurately illustrated, with the disc being much thicker than the film. The sensing composition between the discs and film is of intermediate thickness. In FIGS. 2 and 3, for the sake of illustration clarity, the thicknesses of all of the glass disc, opaque film and sensing composition are shown as being equal.

Referring now to FIG. 1, the disassembled gas sensing element, shown generally at 10, includes a stretched sheet 12 of opaque film, glass discs 14 and 15 and drops 16 and 17 of the sensing composition precursor. As shown in FIG. 1, the drops 16 and 17 of sensing composition precursor are placed on the stretched sheet 12. The glass discs 14 and 15 are then placed on top of the drops 16 and 17, respectively of sensing composition precursor and this precursor is allowed to cure to form the sensing composition. Referring to FIGS. 2 and 3, after being cut from the stretched sheet 12 and trimmed to conform to the circular shape of glass disc 14, the assembled gas sensing element, shown generally at 20, includes an opaque film 21, the sensing composition 22 and the glass disc 14. The sensing composition 22 is secured to both the opaque film 21 and the glass disc 14.

The sensing element 20 is tested and found to have acceptable characteristics for use in a sensor for measuring the concentration of carbon dioxide in blood.

As shown in FIGS. 2 and 3, this assembled gas sensing element 20 is placed into well 24 of sensor holder 26 and bonded in place using a layer 27 of transparent, silicone-based adhesive. Well 24 is open at one end, includes a right circular cylindrical side wall 25 and a circular bottom end wall 28. The size of well 24 is such that the assembled gas sensing element 20 and silicone-based adhesive layer 27 completely fill well 24. Assembled gas sensing element 20 is placed in well 24 so that the glass disc 14 faces the bottom end wall 28 of well 24. The opaque film 12 includes an exposed surface 29 which is raised relative to the inner surface 30 of sensor holder 26. The opaque film 12 substantially shields sensing composition 22 from direct contact with the medium, e.g., blood, to be monitored.

Referring now to FIG. 3 in use sensor holder 26, made of a transparent polycarbonate material is placed in abutting relation to optical fiber 32. Optical fiber 32 provides excitation light of appropriate wavelength from light transmitting apparatus 34 to excite the sensing component in the sensing composition 22 to fluoresce and provide a signal characteristic of the concentration of carbon dioxide located in the medium in contact with the opaque film 12. This optical fiber 32 also transmits the signal which is emitted from the sensing component and passes such signal to a light receiving apparatus 36, which processes or analyzes this emitted signal, e.g., as described in Lubbers et al U.S. Reissue Pat. No. 31,879 and Heitzmann U.S. Pat. No. 4,557,900 36, to determine the concentration of carbon dioxide in this medium. The above-noted Heitzmann patent is incorporated by reference in its entirety herein.

Over a period of time the assembled sensing element 20 provides consistent, e.g., substantially "drift" free, signals which are reliably correlated to the true and accurate concentration of carbon dioxide in the blood in contact with the opaque film 12.

EXAMPLE 2

Example 1 is repeated except that the sensing composition precursor includes a fluorescence oxygen indicator, vinyl terminated dimethylsiloxane and a silicone-based cross-linking agent.

The assembled sensing element produced in Example 2 is used as shown in FIG. 3 and as described above with regard to the carbon dioxide sensing element except that the Example 2 sensing element is used to sense the oxygen concentration in the blood. Over a period of time this Example 2 assembled sensing element provides acceptable signals which are reliably correlated to the true and accurate concentration of oxygen in the blood in contact with the opaque film.

While this invention has been described with respect to various specific examples and embodiments, it is to be understood that the invention is not limited thereto and it can be variously practiced within the scope of the following claims.

What is claimed is:

1. A method for making a gas sensing element useful in sensing the concentration of a gas in a medium comprising:
    placing sensing composition precursor between and in contact with a transparent, gas impermeable solid disc and an opaque, gas permeable film oppositely disposed from said transparent, gas impermeable solid disc, said sensing composition precursor comprising a sensing component and a polymer precursor; and, thereafter,
    forming from said sensing composition precursor sensing composition including gas permeable and light permeable polymeric material and said sensing component, said forming including reacting said polymer precursor.

2. The method of claim 1 wherein said transparent, gas impermeable solid disc is made of glass, and said opaque, gas permeable film includes an opaque agent and a polymer selected from the group consisting of polyfluorohydrocarbons, polyfluorocarbons and mixtures thereof.

3. The method of claim 2 wherein said polymer is polytetrafluoroethylene.

4. The method of claim 1 wherein said sensing composition precursor further includes a cross-linking agent and said gas permeable and light permeable polymeric material is cross-linked.

5. The method of claim 1 wherein said sensing component is dissolved in an aqueous liquid dispersed in said gas permeable and light permeable polymeric material.

6. The method of claim 5 wherein said gas permeable and light permeable polymeric material is substantially ion impermeable, said dispersed aqueous liquid of said sensing composition is buffered and said sensing component is effective to provide a signal which varies as the pH of said dispersed aqueous liquid of said sensing composition varies.

7. The method of claim 6 wherein said dispersed aqueous liquid of said sensing composition has a pH in the range of about 6 to about 8 and the gas sensing element is effective in sensing the concentration of carbon dioxide in blood.

8. The method of claim 5 wherein said sensing composition precursor further includes a hydrophilic dispersing agent in an amount effective to facilitate maintaining said dispersed aqueous liquid in a dispersed state in said sensing composition precursor.

9. The method of claim 8 wherein said hydrophilic dispersing agent is selected from the group consisting of hydroxyalkyl celluloses and mixtures thereof.

10. The method of claim 8 wherein said hydrophilic dispersing agent is hydroxyethyl cellulose.

11. The method of claim 1 wherein said sensing composition is effective in sensing the concentration of oxygen in blood.

12. The method of claim 1 wherein said transparent, gas permeable solid disc has a thickness across two substantially opposing ends only one of which is in contact with said sensing composition precursor in the range of about 0.005 inches to about 0.1 inches.

13. A method for making a plurality of gas sensing elements useful in sensing the concentration of a gas in a medium comprising:
    placing sensing composition precursor in contact with an opaque, gas permeable film, said sensing composition precursor comprising a sensing component and a polymer precursor;
    placing a plurality of transparent, gas impermeable solid discs in contact with said sensing composition precursor; thereafter,
    forming from said sensing composition precursor sensing composition including gas permeable and light permeable polymeric material and said sensing component, said forming including reacting said polymer precursor; and
    forming individual gas sensing elements each of which includes one of said transparent, gas impermeable solid discs, a portion of said sensing composition and a portion of said film.

14. The method of claim 13 wherein said transparent, gas impermeable solid discs are made of glass, and said opaque, gas permeable film includes an opaque agent and a polymer selected from the group consisting of polyfluorohydrocarbons, polyfluorocarbons and mixtures thereof.

15. The method of claim 14 wherein said polymer is polytetrafluoroethylene.

16. The method of claim 13 wherein said sensing composition precursor further includes a cross-linking agent and said gas permeable and light permeable polymeric material is cross-linked.

17. The method of claim 13 wherein each of said plurality of transparent, gas permeable solid discs has a thickness across two substantially opposing ends only one of which is in contact with said sensing composition precursor in the range of about 0.005 inches to about 0.1 inches.

18. A method for making a sensor useful in sensing the concentration of a gas in a medium comprising:

placing sensing composition precursor between and in contact with a transparent, gas impermeable solid disc and an opaque, gas permeable film, said sensing composition precursor comprising a sensing component and a polymer precursor; thereafter forming from said sensing composition precursor sensing composition including gas permeable and light permeable polymeric material and said sensing component, said forming including reacting said polymer precursor, the combination comprising said sensing composition, said transparent, gas impermeable solid disc and said opaque, gas permeable film being referred to as a sensing element; and placing said sensing element at least partially in a cavity having an open end and being located in a substantially transparent sensor holder so that said opaque, gas permeable film is exposed to the medium.

19. The method of claim 18 which further comprises testing said sensing element for efficacy in sensing the concentration of a gas in a medium prior to said sensing element placing step.

20. The method of claim 18 which further comprises securing said sensing element to said substantially transparent sensor holder.

21. The method of claim 18 wherein said sensing component is dissolved in an aqueous liquid dispersed in said gas permeable and light permeable polymeric material.

22. The method of claim 21 wherein said gas permeable and light permeable polymeric material is substantially ion impermeable, said dispersed aqueous liquid of said sensing composition is buffered and said sensing component is effective to provide a signal which varies as the pH of said dispersed aqueous liquid of said sensing composition varies.

23. The method of claim 22 wherein said dispersed aqueous liquid of said sensing composition has a pH in the range of about 6 to about 8 and the gas sensing element is effective in sensing the concentration of carbon dioxide in blood.

24. The method of claim 18 wherein the gas sensing element is effective in sensing the concentration of oxygen in blood.

25. The method of claim 18 wherein said solid disc has a thickness across two substantially opposing ends only one of which is in contact with said sensing composition precursor in the range of about 0.005 inches to about 0.1 inches.

* * * * *

UNITED STATES PATENT AND TRADEMARK OFFICE
CERTIFICATE OF CORRECTION

PATENT NO. : 5,175,016

DATED : December 29, 1992

INVENTOR(S) : Masao Yafuso et al.

It is certified that error appears in the above-identified patent and that said Letters Patent is hereby corrected as shown below:

Column 13:

In claim 18, line 7, after "thereafter" insert a comma.
Column 14:
In claim 25, line 1, after "said" insert --transparent, gas permeable--.

Signed and Sealed this

Thirtieth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,175,016
DATED : December 29, 1992
INVENTOR(S) : Masao Yafuso, Mark Z. Holody, Thomas P. Maxwell, Thomas G. Hacker It is certified that error appears in the above-indentified patent and that said Letters Patent is hereby corrected as shown below:

Column 12, claim 17, line 66, after "gas" change "permeable" to --impermeable--, Column 14, claim 25, line 1, after "transparent, gas" change "permeable" to --impermeable-- .

Signed and Sealed this

Twenty-ninth Day of May, 2001

Attest:

NICHOLAS P. GODICI

*Attesting Officer*  *Acting Director of the United States Patent and Trademark Office*